United States Patent [19]

Klein et al.

[11] Patent Number: 4,488,877
[45] Date of Patent: Dec. 18, 1984

[54] PERCUTANEOUS IMPLANT FOR PERITONEAL DIALYSIS

[75] Inventors: Elias Klein; Ronald L. Wathen; Richard A. Ward, all of Louisville, Ky.; Louis C. Cosentino, Wayzata, Minn.; Larry E. Fuller, Minnetonka, Minn.; Felix J. Martinez, Plymouth, Minn.

[73] Assignee: Renal Systems, Inc., Minneapolis, Minn.

[21] Appl. No.: 410,365

[22] Filed: Aug. 23, 1982

[51] Int. Cl.³ .............. A61F 1/00; A61M 25/02
[52] U.S. Cl. .......................... 604/175; 604/244
[58] Field of Search .................... 604/8–10, 604/28, 29, 175, 244, 891; 128/1 R

[56] References Cited

U.S. PATENT DOCUMENTS

| | | | |
|---|---|---|---|
| 3,402,710 | 9/1968 | Paleschuck | 128/1 R |
| 3,447,161 | 6/1969 | Weikel | 128/334 C X |
| 3,783,868 | 1/1974 | Bokros | 604/175 X |
| 4,416,657 | 11/1983 | Berglund | 604/175 X |
| 4,417,888 | 11/1983 | Cosentino et al. | 604/175 |

Primary Examiner—Dalton L. Truluck
Attorney, Agent, or Firm—Schroeder, Siegfried, Vidas & Arrett

[57] ABSTRACT

An implant device for peritoneal dialysis which permits a flexible catheter to be removed and replaced without invasive surgery. The catheter is passed through a substantially rigid tubular percutaneous device and a flexible sleeve member which together form a continuous conduit from the body exterior through the peritoneal wall. The catheter is associated with a percutaneous tubular device so as to be removable and replaceable through the sleeve member after implantation. The catheter preferably has a relatively weak memory which gives it a tendency to maintain a compact coiled configuration near the peritoneal wall. The catheter may extend through the percutaneous device or, more preferably, terminates within the interior cavity of the percutaneous device and is sealed from the environment by means of a septum closure within the device cavity.

8 Claims, 3 Drawing Figures

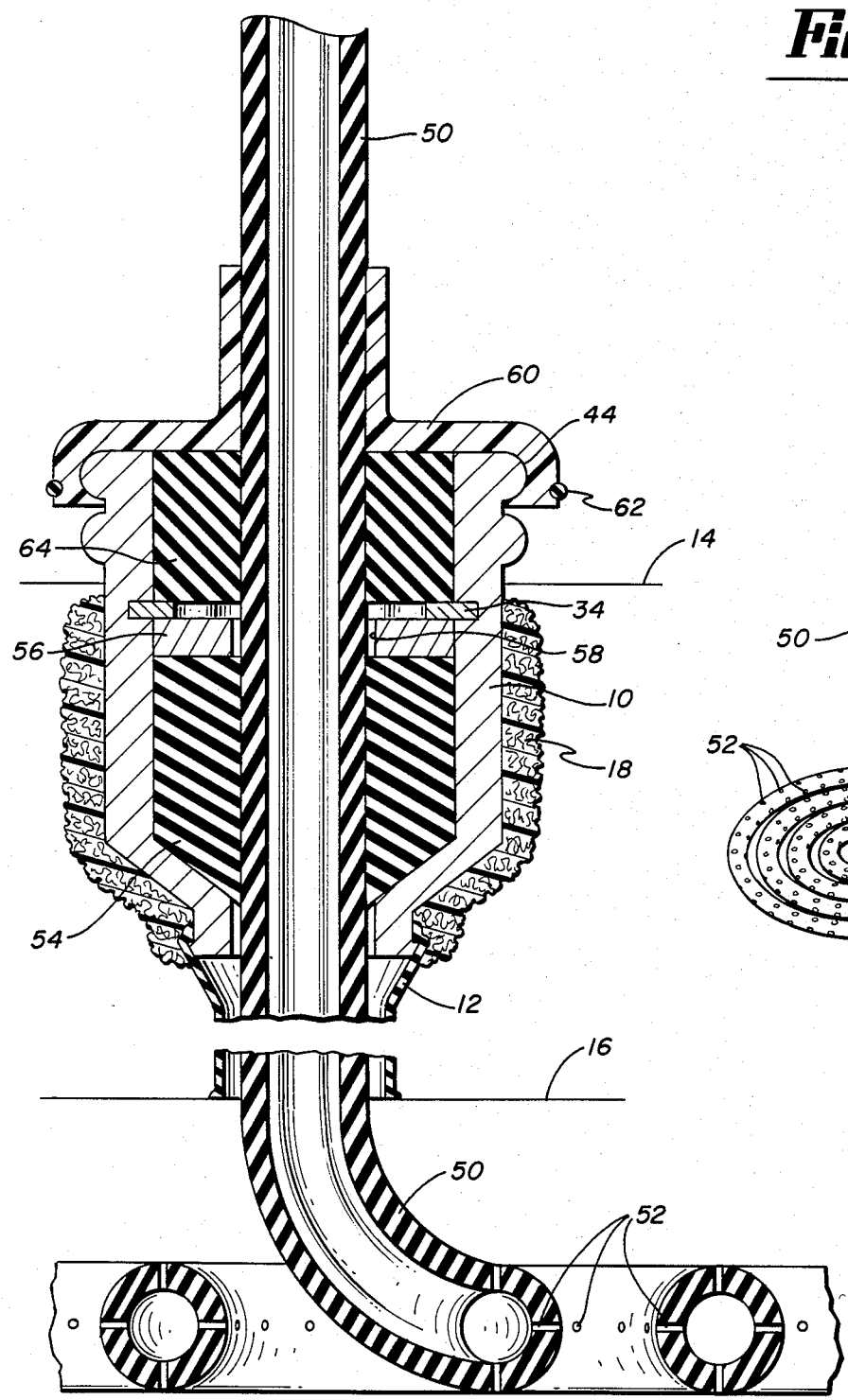

PERCUTANEOUS IMPLANT FOR PERITONEAL DIALYSIS

BACKGROUND OF THE INVENTION

Peritoneal dialysis is accomplished by means of a flexible catheter implanted so as to pass directly through the skin and peritoneal wall into the peritoneal cavity. In its most common practice, continuous peritoneal dialysis involves connecting the body exterior end of the catheter to a plastic bag of dialysate solution which is drained into the peritoneal cavity. The bag and catheter connecting tubes are wrapped around the body of the patient during the dialysis interval, remaining connected to the catheter. At the end of the dialysis interval, the bag is dropped and the used dialysate is drained back into the bag by gravity. After drainage is completed, a fresh bag of dialyzate is connected to the catheter and the cycle repeated. A recent detailed review of devices associated with peritoneal dialysis may be found in Ward et al, "Investigation of the Risks and Hazards with Devices Associated with Peritoneal Dialysis (including Intermittant Peritoneal Dialysis and Continuous Ambulatory Peritoneal Dialysis) and Sorbent Regenerated Dialysate Delivery Systems", Revised Draft Report for FDA Contract No. 223-81-5001 (June 1982).

Despite extensive protocols for maintaining sterility, infection frequently occurs as a result of peritoneal dialysis. The most common infection pathway is through the interior of the catheter but exit site infection caused by bacteria invasion along the exterior surfaces of the catheter occurs as well.

Improvements in peritoneal dialysis implants are described in co-pending applications Ser. No. 314,569, filed 10/26/81 U.S. Pat. No. 4,417,888, issued Nov. 29, 1983 which have a common assignee with the present application. The improvements of these prior applications comprise rigid tubular percutaneous devices implanted through the skin to which a catheter member is affixed subcutaneously. The percutaneous devices of these applications are preferably septum closed with access to the peritonium accomplished through a sterile needle assembly. The rigid tubular configuration of the percutaneous device provides substantial benefits in minimizing exit site infection, in part, by providing a structure less subject to attack by body fluids. The percutaneous device is preferably made of titanium which may be coated with vapor deposited carbon or other biocompatible coatings. The preferred septum closure of these devices together with needle access provides an improved infection barrier through the interior of the device. The septum closure is especially advantageous in eliminating most risk of infection through accidental disconnection or damage to the catheter connections. When the needle is removed either accidentally or between dialysis cycles, the septum automatically closes maintaining the aseptic condition. The closure is below the skin reducing the possibility of damage to the catheter portion of prior devices which extend through the skin for an inch or more.

BRIEF DESCRIPTION OF THE INVENTION

The present invention provides further improvements on implantable devices for peritoneal dialysis similar to those of the aforementioned prior patent applications. The invention in its various embodiments permits a flexible peritoneal dialysis catheter to be removed and replaced without invasive surgery. This is accomplished by passing the catheter through a substantially rigid tubular percutaneous device of biologically compatible material which extends through the skin when implanted so as to provide means for accessing the body interior through the interior of said device. The flexible catheter member is associated with the percutaneous tubular device for providing fluid communication between the body exterior and the peritoneal cavity through the tubular percutaneous device. The invention includes a flexible sleeve member of biologically compatible material surrounding the catheter for a portion of the length thereof from the percutaneous tubular device. The length of the sleeve is sufficient to pass through the tissue between the percutaneous device and the peritoneal wall. The sleeve includes a free end which may be affixed to the peritoneal wall around an opening therein by surgical adhesive or suture so as to provide a conduit between the percutaneous device and the peritoneal cavity through which the catheter is carried into the peritoneal cavity. The catheter member is associated with the percutaneous tubular device so as to be removable and replaceable through the sleeve member after implantation. The sleeve is preferably made of a biologically compatible polymeric material which has sufficient porosity to permit tissue in-growth therein but insufficient porosity to permit substantial leakage of peritoneal fluids into the tissue surrounding the sleeve. A further improvement is to provide the flexible catheter with a memory so that it has a tendency to maintain a compact, coiled configuration near the peritoneal wall. The catheter also preferably has a closed distal end and a plurality of small holes in the sides thereof on the portion which extends into the peritoneal cavity.

Whereas one embodiment of the present invention employs a catheter which extends from the peritoneal cavity through the flexible sleeve and percutaneous device to a standard connector on the exterior side of the body, it is preferred that the catheter extend only into the rigid percutaneous device and that the end of the catheter be configured so as to accommodate a septum closure. This preferred configuration allows the advantages of the present invention to be combined with those of the previous aforementioned applications.

BRIEF DESCRIPTION OF THE DRAWINGS

FIG. 2 is a cross-sectional view of an alternate embodiment of the invention adaptable for conventional peritoneal dialysis connections.

FIG. 3 is a pictoral view of the catheter of FIG. 2 showing the preferred coiled configuration.

DETAILED DESCRIPTION OF THE INVENTION

Figure 1:
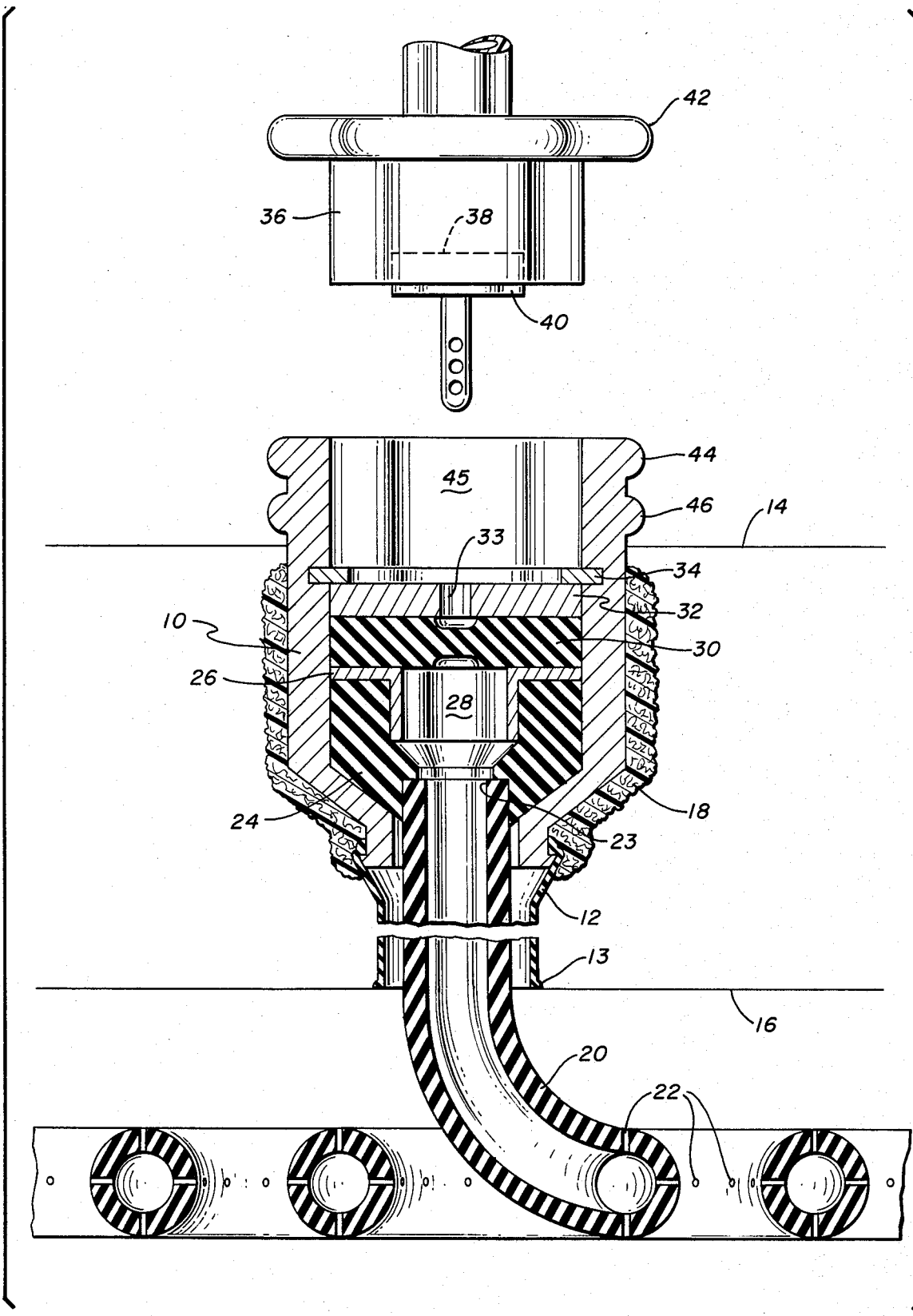
FIG. 1 is a cross-sectional view of the preferred septum closed embodiment of the invention together with a needle assembly shown in side view.

The preferred embodiment of the invention is shown in FIG. 1. A rigid tubular device 10 and attached flexible sleeve member 12 including distal end 13 are implanted between the skin layer 14 and the peritoneal wall 16. The distal end 13 of sleeve 12 is surgically attached to an opening in the peritoneal wall so as to provide a continuous, permanent conduit between the peritoneal cavity and the exterior of the body. Device 10 is preferably made of titanium which may be coated with vapor deposited carbon or other biocompatible coatings. Alternatively, device 10 may remain uncoated. Flexible sleeve member 12 is preferably made of a material such as expanded polytetrafluoroethylene sold under the trade name Gor-Tex by W. L. Gore Company of Newark, Del. This expanded polytetrafluoroethylene material permits some tissue ingrowth stabilizing the sleeve but is insufficiently porous to allow significant leakage of dialysate into the surrounding tissue.

Below the skin line 14 a porous velour cuff member 18 is preferably affixed to device 10 so as to surround both device 10 and the joint between device 10 and sleeve 12. Cuff 18 is preferably made of Dacron ® (polyethyleneterephthalate). The Dacron cuff serves as a tissue ingrowth media which stabilizes the implant and prevents extrusion. As an alternative to use of a Dacron cuff, a porous titanium coating on device 10 may be used. Such coatings are described for similar devices used in blood access applications in U.S. Pat. No. 4,405,319, which issued Sept. 20, 1983, to Cosentino, the disclosure of which is incorporated herein by reference.

Sleeve 12 provides a conduit through which a flexible catheter member 20 may be inserted into the peritoneal cavity. Catheter 20 includes a plurality of small holes 22 in the portion of the catheter which extends into the peritoneal cavity. Holes 22 should have a combined cross-sectional area greater than the cross-sectional area of the catheter itself so as to assure that the flow velocity of the dialysis fluid into and out of the peritoneal cavity is low. Catheter 20 also preferably has a closed distal end to assure that the liquid flow occurs through the side holes so as to maintain the low flow velocity. The catheter may be made of medical grade silicone elastomers commonly used in prior art peritoneal dialysis catheters. It is preferred that the catheter be manufactured as described below so as to include a memory of a coiled configuration while maintaining flexibility.

The proximal end portion 23 of catheter 20 is joined to a plug member 24 also preferably made of silicone elastomer. The plug member 24 may alternatively be manufactured as part of the original catheter. Plug member 24 is configured so as to sealably conform to the interior bottom and sides of tubular member 10. A rigid flange member 26 defines an opening 28 in the plug member which provides connection to the interior of channel of catheter 20. The upper surface of flange member 26 provides a rigid seat for a septum closure 30 which provides interruptable seal means between the exterior of the body and the body interior. Septum 30 is held in place by a rigid pressure plate 32, which defines an opening 33 therethrough, and by retaining ring 34. Details of preferred septum constructions and alternative septum retaining means are disclosed in co-pending application, Ser. No. 314,569, filed 10/26/81 and U.S. Pat. Nos. 4,417,888 and 4,405,320 the disclosures of which are incorporated herein by reference.

The preferred septum closed embodiment to FIG. 1 is designed to be accessed by means of a needle assembly 36, shown in FIG. 1 in side view. Assembly 36 preferably includes a recess 38 which retains a sponge 40. Sponge 40 may be saturated with an antiseptic solution such as Betadine ® (polyvinylpyrollidone/iodine solution) for maintaining sterility within the cavity of device 10.

A ridge 42 on needle assembly 36 and a second ridge 44 on device 10 provide gripping surfaces for a clip (not shown) to hold the assembly securely in place during dialysis. Between dialysis intervals, a plastic cap member (not shown) may be slipped over ridge 44. In such case, a Betadine saturated sponge is preferably included within the cavity 45 of device 10.

The second ridge 46 between the skin line and ridge 44 is preferably provided on device 10 so that the device may be held by means of a forceps during implantation and needle change operations. A suitable forceps tool for gripping ridge 44 is described in co-pending application, Serial No. 209,058, filed 11/21/80, the disclosure of which is incorporated herein by reference.

FIG. 2 shows a modified embodiment of the present invention. The embodiment of FIG. 2 includes a rigid, tubular percutaneous structure 10, flexible sleeve 12 and Dacron collar 18 identical to the structures of FIG. 1. Catheter 50, however, is modified so as to pass through device 10 connecting by conventional means to a dialysate bag or dialysis machine. This is accomplished by molding or adhesively fixing a silicone plug member 54 to catheter 50. Plug 54 is configured so as to sealably contact the interior walls and bottom of device 10 when a pressure plate 56 and retaining ring 34 are in place. The pressure plate 56 defines an opening 58 therethrough, through which catheter 50 passes. A cap member 60 is associated with catheter 50 by friction fit or adhesive bonding. Cap 60 is made of a flexible plastic and is configured so as to sealably snap over ridge 44. An O-ring or clip member 62 holds cap 60 in place. A Betadine saturated sponge 64 fills the recess above retaining ring 34 so as to provide an additional bacterial barrier.

FIG. 3 shows a preferred coiled configuration of the catheter 50 and holes 52. The memory which holds the catheter in the coiled configuration should be sufficiently weak that the catheter can be held in a straightened configuration by a thin wire inserted therethrough. In that way the catheter may be inserted and withdrawn readily through device 10 and sleeve 12. By providing device 50 with a memory in a coiled configuration, however, the tendency of the catheter to wander throughout the peritoneal cavity and the problems associated with that tendency are reduced.

The principal advantage of the present invention is the removability of the catheter without invasive surgery. A major problem encountered with peritoneal dialysis catheters is the clogging of the catheter which eventually requires replacement of the catheter. Permanent obstruction can result from encapsulation of the catheter by fibrous adhesions or the omentum. One way flow obstruction also frequently occurs for a variety of reasons including the formation of omentum flaps over the drainage holes. Obstruction is a common cause of removal of catheters which have good skin tunnels and an absence of infection. The present invention permits catheter replacement to be accomplished without invasive surgery because the catheter itself is not embedded in any body tissue. Instead, the combination of the rigid, percutaneous implant and the flexible polymeric sleeve provides a permanently implanted conduit through which the catheter may be inserted into the peritoneal cavity and removed therefrom.

The removability of the catheter is also advantageous in instances where the patient contacts peritonitis as a result of a bacterial invasion through the catheter in which the bacterial colony lodges in the catheter itself.

The coiled configuration of the catheter portion within the peritoneal cavity near the entrance site into the cavity permits placement of the catheter for more efficient drainage. Whereas previous catheters were free to wander through the peritoneal cavity, sometimes resulting in placement where gravity drainage is difficult if not impossible, the memory in the catheters of the present invention tends to keep the entire catheter in one location near the implant site.

What is claimed is:

1. In an improved percutaneous implant especially suitable for peritoneal dialysis applications, the implant comprising:

a substantially rigid tubular percutaneous device of biologically compatible material which extends through the skin when implanted so as to provide means for accessing the body interior through the interior of said device, and a flexible subcutaneous catheter member associated with said percutaneous tubular device for providing fluid communication between the body exterior and the peritoneal cavity, the improvement comprising:

a flexible sleeve member of biologically compatible material surrounding said catheter for a portion of the length thereof from said percutaneous tubular device, the length of the sleeve being sufficient to pass through the tissue between said percutaneous device and through the peritoneal wall, said sleeve including a free end affixable to the peritoneal wall around an opening therein and a fixed end connected to said rigid tubular percutaneous device so as to provide a conduit between said percutaneous tubular device and the peritoneum through which said catheter is carried into the peritoneum; and said catheter member being removably engaged within said percutaneous tubular device and said sleeve member so as to be removable and replaceable through said sleeve member after implantation.

2. An improved percutaneous implant in claim 1 wherein the sleeve member is made of a material sufficiently porous to permit tissue ingrowth therein but insufficiently porous to permit significant leakage of peritoneal fluids through the sleeve member into the surrounding tissue.

3. A percutaneous implant as in claim 2 wherein the sleeve member is made of an expanded polytetrafluoroethylene.

4. A percutaneous implant as in claims 1 or 2 wherein the catheter member includes a plurality of perforations through the side walls thereof.

5. A percutaneous implant as in claim 4 wherein the distal end of the catheter is closed.

6. A percutaneous implant as in claim 4 wherein the catheter member is of a flexible material having a memory in a coiled configuration on the portion of the catheter within the peritoneal cavity when implanted.

7. A percutaneous implant as in claim 1 wherein said catheter member extends through said tubular percutaneous device and includes a plug member surrounding a portion of the catheter passing through said percutaneous device, the plug member configured so as to sealably contact the interior surfaces of the tubular percutaneous device.

8. A percutaneous implant as in claim 1 wherein said catheter member terminates within said tubular percutaneous device and includes on the proximal end thereof a plug member conforming to the interior surfaces of said percutaneous device, and wherein said implant includes a septum closure above said plug member in sealed relationship therewith.

* * * * *